(12) United States Patent
Chang et al.

(10) Patent No.: US 6,388,265 B1
(45) Date of Patent: May 14, 2002

(54) METHOD FOR DISTINGUISHING A SPECIFIC REGION IN A SAMPLE TO BE OBSERVED BY A MICROSCOPE

(75) Inventors: Wen-Tung Chang; Jui-Yen Huang, both of Hsinchu (TW)

(73) Assignee: Mosel Vitelic, Inc. (TW)

( * ) Notice: Subject to any disclaimer, the term of this patent is extended or adjusted under 35 U.S.C. 154(b) by 0 days.

(21) Appl. No.: 09/430,945

(22) Filed: Nov. 1, 1999

(30) Foreign Application Priority Data

Nov. 2, 1998 (TW) .......................................... 87118216

(51) Int. Cl.$^7$ .............................................. G01N 21/86
(52) U.S. Cl. ............................... 250/559.44; 250/559.33
(58) Field of Search ........................ 250/559.44, 559.33, 250/559.4, 201.3, 306, 307, 492.1, 492.2, 492.3

(56) References Cited

U.S. PATENT DOCUMENTS 5,990,478 A * 11/1999 Liu ............................ 250/307

* cited by examiner

*Primary Examiner*—Que T. Le
(74) *Attorney, Agent, or Firm*—Peter F. Corless; Steven M. Jensen; Edwards & Angell, LLP

(57) ABSTRACT

A method for distinguishing a specific region in a sample to be observed by a microscope is disclosed. The method includes the steps of (a) forming a first concavity on a first side of the specific region by a focus ion beam (FIB) technique, (b) forming a second concavity on a second side of the specific region opposite to the first side by the focus ion beam technique, and (c) filling the first concavity and the second concavity with a first metallic packing and a second metallic packing respectively for defining the specific region to be observed.

14 Claims, 4 Drawing Sheets

METHOD FOR DISTINGUISHING A SPECIFIC REGION IN A SAMPLE TO BE OBSERVED BY A MICROSCOPE

FIELD OF THE INVENTION

The present invention is related to a marking method for preparing a specimen, and more particularly to a method for distinguishing a specific region in a sample to be observed by a microscope applied in preparing an ultra-thin specimen.

BACKGROUND OF THE INVENTION

Nowadays, due to the improvement in the manufacturing process of the microelectronic element and tendency of demanding a smaller line width, the semiconductor analysis is getting more and more difficult, particularly in the analysis technology of the finished dynamic random access memory (DRAM) having a size less than 0.25 $\mu$m.

In the semiconductor industry, it is common to use a scanning electron microscopy (SEM) to observe the surface condition of a wafer and use a transmission electron microscopy (TEM) to examine the microstruture of a wafer to ensure that the fabricated microelectronic elements satisfy an expected standard. However, because the resolution of the scanning electron microscope (SEM) is not good enough to observe the detailed structure of the mirocelectronic elements, it is replaced by the transmission electron microscope (TEM) to make major failure analysis. As one may realize, most of the problems in TEM application are related to sample preparation, which is the most difficult part of TEM analysis. Traditionally, a sample is cut from a wafer to be examined. After thoroughly polished, the sample becomes ultra-thin and is ready to be examined by the transmission electron microscope (TEM) for determining the quality of the wafer. However, during the preparing process, an optical microscope and a suitable marking method for the sample must be employed so that an ultra-thin specimen for fixed-point failure analysis can be prepared easily.

At the present time, a conventional method for marking a specific region in a sample utilizes a laser technique. However, the laser cannot be focused further so that the width of the mark made by the laser technique is many times than 0.25 $\mu$m. Due to the resolution limitation of the optical microscope, a single-bit failure analysis cannot be carried out by employing the laser technique to prepare the specimen. Hence, a focus ion beam technique (FIB) was designed to make TEM sample instead of the laser technique. The focus ion beam (FIB) technique utilizes focused high-energy gallium ions to remove materials from both sides of the desired region. The focus ion beam (FIB) technique can offer a reliable method to precisely obtain a cross section of the specific area, and the sample can be thined to less than 0.1 $\mu$m. However, this method requires very expensive equipment and cost for preparing an ultra-thin specimen, which further limits the usage of this method. Therefore, it is not worthy to prepare an ultra-thin specimen directly by the focus ion beam (FIB) technique.

For the above reason, it is desirable to develop a low-cost and effective method for preparing an ultra-thin specimen of 0.25 $\mu$m or less size dynamic random access memory (DRAM).

SUMMARY OF THE INVENTION

It is therefore a primary object of the present invention to provide a effective method for distinguishing a specific region in a sample to be observed by a microscope so that an ultra-thin specimen can be prepared easily.

Another object of the present invention is to provide a specific metallic mark "==" formed in the sample for distinguishing a specific region to be observed by a microscope during the preparing process so that the sample can be polished to a required thickness.

It is further another object of the present invention to provide an effective marking method for distinguishing a specific region in a sample by a focus ion beam technique so as to avoid unnecessary damage for the ultra-thin specimen and reduce the cost for preparing the ultra-thin specimen.

In order to accomplish the object of the present invention, a method for distinguishing a specific region in a sample to be observed by a microscope is provided. The method includes the steps of (a) forming a first concavity on a first side of the specific region by a focus ion beam (FIB) technique, (b) forming a second concavity on a second side of the specific region opposite to the first side by the focus ion beam technique, and (c) filling the first concavity and the second concavity with a first metallic packing and a second metallic packing respectively for defining the specific region to be observed. Preferably, the method further includes the steps of forming a third concavity on the first side of the specific region and a fourth concavity on the second side of the specific region, and then filling the third concavity and the fourth concavity with a third metallic packing and a fourth metallic packing respectively.

In accordance with one aspect of the present invention, the first concavity and the third concavity are positioned between the second concavity and the fourth concavity.

In accordance with another aspect of the present invention, the first concavity is positioned between the second concavity and the fourth concavity, and the fourth concavity is positioned between the first concavity and the third concavity.

In accordance with another aspect of the present invention, after the step (c), the method further includes a step of (d1) polishing the first side of the sample at a relatively higher polishing rate till the first metallic packing is partially polished. Then, after the step (d1), the method further includes a step of (d2) polishing the first side of the sample at a relatively lower polishing rate till the first metallic packing is completely polished.

In accordance with another aspect of the present invention, after the step (d2), the method further includes a step of (d3) stopping polishing the first side of the sample and then polishing the other side of the sample.

Preferably, the step (c) is executed by a sputtering technique.

Preferably, the microscope is one selected from the group consisting of an optical microscope (OM), a transmission electron microscope (TEM), and a scanning electron microscope (SEM).

Preferably, each of the metallic packings is made of one selected from Platinum (Pt) and Tungsten (W).

Preferably, each of the concavities is substantially a parallelepiped having a length larger than 2 $\mu$m, a width ranged from 1 to 2 $\mu$m, and a depth ranged from 3 to 5 $\mu$m.

Preferably, each of the concavities is extended to a silicon substrate under the specific region of the sample.

Preferably, the distance between the first concavity and the third concavity is larger than 2 $\mu$m.

Preferably, the specific region has a width of about 0.5 $\mu$m.

A still further object of the present invention is to provide a method for distinguishing a specific region in a sample to be observed by a microscope. The method includes steps of (a) forming a first receptacle on a first side of a specific region, (b) forming a second receptacle on a second side of the specific region opposite to the first side, and (c) filling a first packing and a second packing respectively in the first receptacle and the second receptacle for defining the specific region to be observed.

The present invention may best be understood through the following description with reference to the accompanying drawings, in which:

DETAILED DESCRIPTION OF THE PREFERRED EMBODIMENTS

Figure 1:
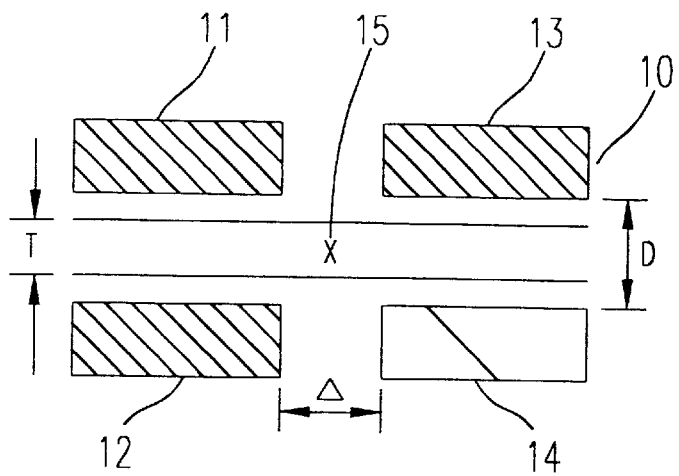
FIG. 1 is a plane view showing a first preferred embodiment of the present invention.

Please refer to FIG. 1 showing a first preferred embodiment of the present invention. As shown in FIG. 1, the prevent invention provides a method for marking a specific region in a sample 10 to be observed by a microscope, which can be applied in preparing an ultra-thin specimen. The marking method of the present invention includes following steps. Firstly, a first concavity 11 is formed on a first side of the specific region in the sample 10 by a force ion beam technique. Secondly, a second concavity 12 is formed on a second side of the specific region opposite to the first side by the force ion beam technique. Then, a first metallic packing and a second metallic packing are sputtered in the first concavity 11 and the second concavity 12 respectively for defining the specific region to be observed. In addition, the method may further include a step of forming a third concavity 13 on the first side of the specific region and a fourth concavity 14 on the second side of the specific region. A third metallic packing and a fourth metallic packing are also sputtered in the third concavity 13 and the fourth concavity 14 respectively. Certainly, the specific region defined by those metallic packings includes the analyzed target 15.

Figure 2:
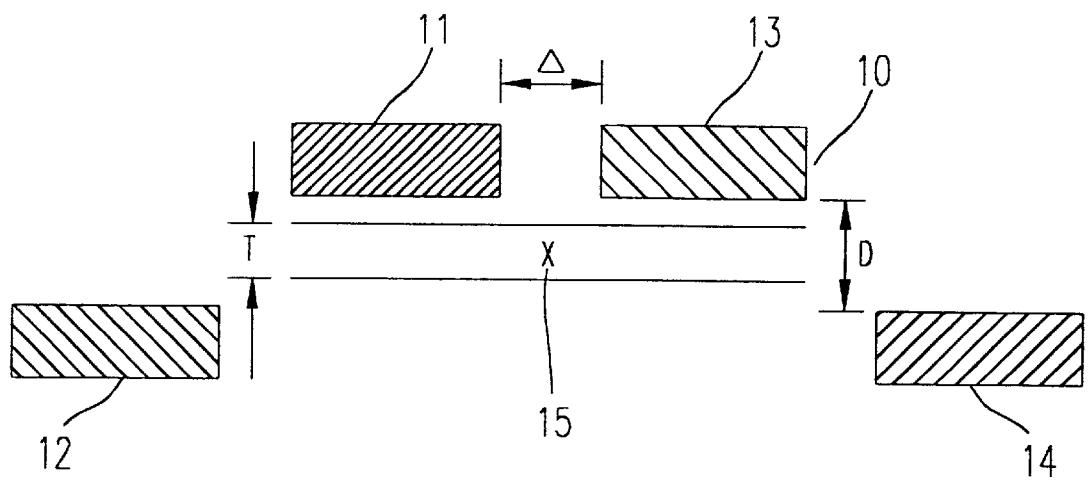
FIG. 2 is a plane view showing a second preferred embodiment of the present invention.
Figure 3:
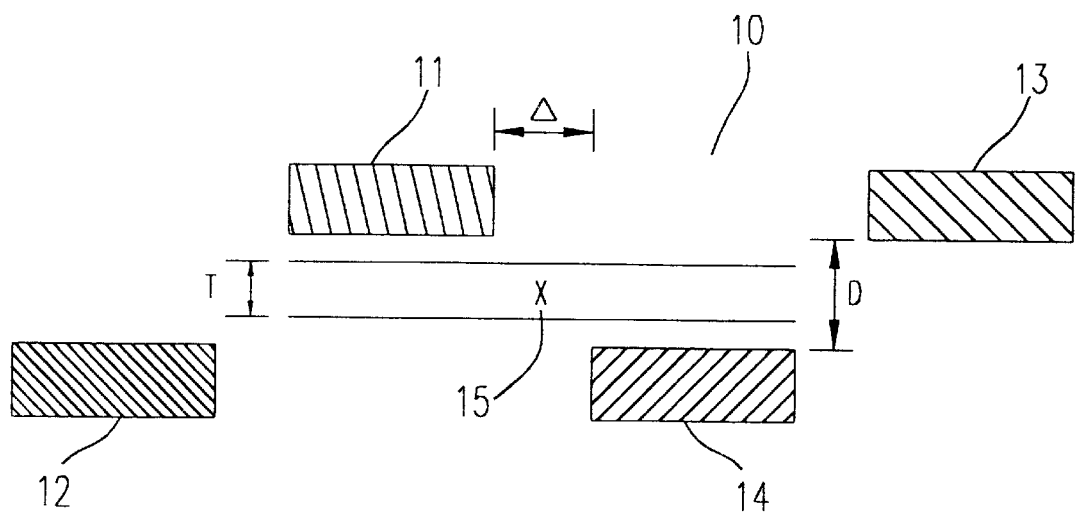
FIG. 3 is a plane view showing a third preferred embodiment of the present invention.

Please refer to FIG. 2 showing a second preferred embodiment of the present invention. As shown in FIG. 2, the first concavity 11 and the third concavity 13 may be positioned between the second concavity 12 and the fourth concavity 14. Please refer to FIG. 3 showing a third preferred embodiment of the present invention, wherein the first concavity 11 may also be positioned between the second concavity 12 and the fourth concavity 14, and the fourth concavity 14 may be positioned between the first concavity 11 and the third concavity 13. Certainly, a fixed points which represents the analyzed target is positioned in the central part of the specific region.

Figure 4:
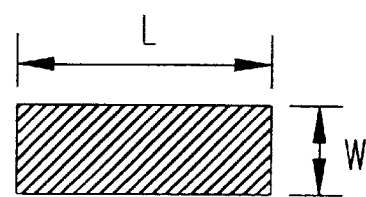
FIG. 4 is a plane view showing one of the metallic packings in FIG. 3.

Please refer to FIGS. 1, 2 and 3 again. The specific region defined by those metallic packings in the sample 10 has a width D of about 0.5 $\mu$m. Preferably, the distance $\Delta$ is larger than 2 $\mu$m. Please refer to FIG. 4 showing a plane view of one of the metallic packings in FIGS. 1, 2, and 3. The metallic packing is sputtered in one of the concavities 11~14. Each of the concavities 11~14 is a parallelepiped-shape concavity having a length L larger than 2 $\mu$m, a width W ranged from 1 to 2 $\mu$m, and a depth ranged from 3 to 5 $\mu$m or smaller than 5 $\mu$m (not shown in FIG. 4). Preferably, the metallic packing is made of one selected from Platinum (Pt) and Tungsten (W).

Figure 5:
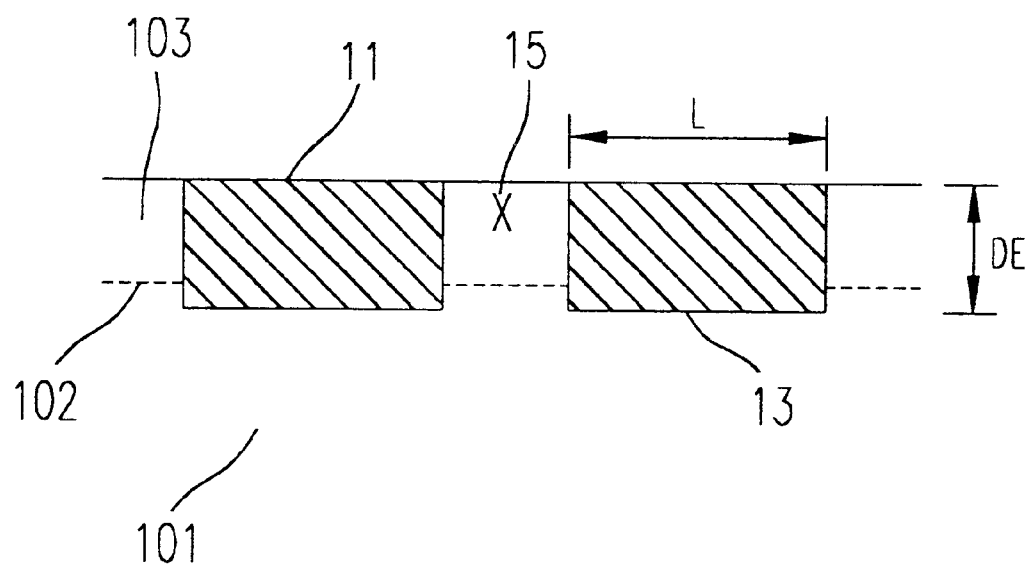
FIG. 5 is a cross-sectional view of FIG. 1.

Please refer to FIG. 5 showing a cross-sectional view of FIG. 1. As shown in FIG. 5, the sample 10 includes a silicon substrate 101. In fact, the depths of those metallic packings are the same as those of the concavities 11~14, depending on the depth of the device. The depths (DE) of those concavities 11~14 must be extended to over that of the device, that is, the depths (DE) of those concavities 11~14 must be extended to the silicon substrate 101 under the interface 102 between the silicon substrate 101 and a deposited material 103. Hence, the depths of those concavities 11~14 can be changed along with various microelectronic elements. However, the most important requirement of the marking method is that the depths (DE) of those concavities must be extended to the silicon substrate 101 under the interface 102 between the silicon substrate 101 and the deposited material 103, and those concavities 11~14 must be fully filled with those metallic packings respectively. Hence, the specific region including the analyzed target 15 in the sample 10 can be observed easily by a microscope during the preparing process to avoid the formation of cracks in the TEM sample due to the local stress during the polishing process. Certainly, the microscope can be one of the optical microscope (DM), the transmission electron microscope (TEM), or the scanning electron microscope (SEM).

Please refer to FIG. 5 again. The shadow portion represents the first and the third metallic packings. Due to the resolution limitation of the optical microscope in top view, the depths of those concavities 11~14 become more important. A required depth of those concavities is not less than 1 $\mu$m (as mentioned above, the depth of the concavities must be extended to over the depth of the device). After defining the specific region in the sample, a milling technique is used to mill the first side of the sample. When the operator observes the first metallic packing and the third metallic packing on the first side of the sample 10, the milling process must be stopped and a polishing process must be executed continuously. Preferably, the polishing process is carried out by using a 0.05 $\mu$m diamond, $Al_2O_3$ or $SiO_2$ particles. During the polishing process, the first side of the sample 10 can be polished at a higher polishing rate till the first metallic packing and the third metallic packing is partially polished. Then, the first side of the sample can be polished at a lower polishing rate till the first metallic packing and the third metallic packing are completely polished. After completely polishing the first metallic packing and the third metallic packing on the first side of the sample, another side of the sample can also be milled and polished in the same steps. As a result of the polishing process, the sample 10 has a thickness T ranged from 0.2 to 0.5 $\mu$m which is suitable for the application of the TEM. Certainly, if possible, the thickness T of the sample 10 can be reduced to less than 0.2 $\mu$m so as to make the fixed-point failure analysis more effective.

Figure 6:
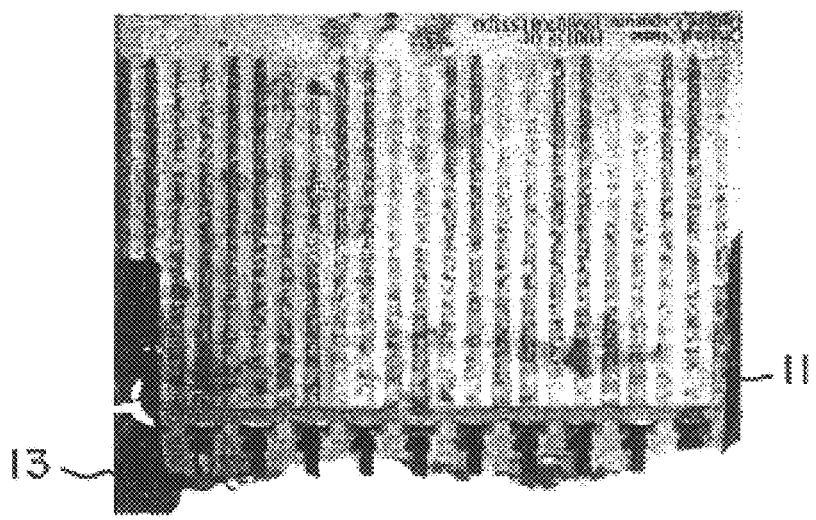
FIG. 6 is a low-magnification image of a TEM specimen during the preparing process.

Please refer to FIG. 6 showing a low-magnification optical image of a TEM specimen during the preparing process. The image shows that the first concavity 11 and the third concavity 13 are respectively formed on both sides of the failure contact chain.

Figure 7:
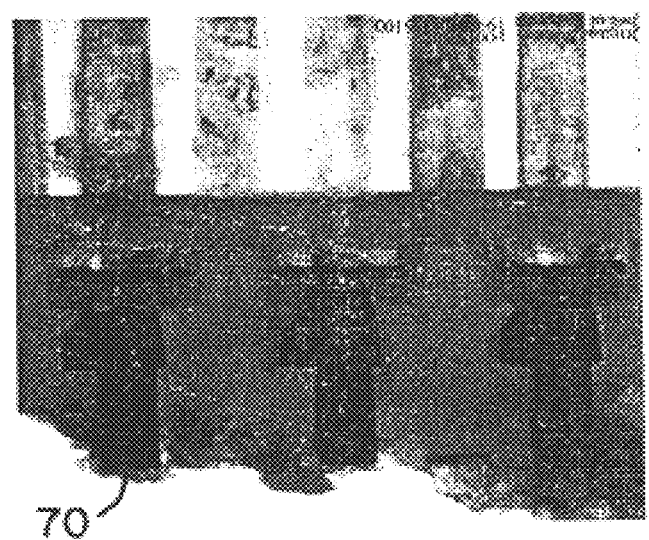
FIG. 7 is a high-magnification image of a finished TEM specimen.

Please refer to FIG. 7 showing a high-magnification image of the finished specimen. This image shows a detailed structure of a W-plug contact open 70 between the first metal layer and the GC word line.

In addition, during the polishing process, the sample must be observed by an optical microscope. Generally, the resolution of the optical microscope in top view is about 0.20~0.5 $\mu$m. If the metallic packings can not be easily observed by the optical microscopy in top view during the polishing process, the length of the concavities 11~14 can be enlarged.

According to the description with reference to the accompanying drawings, the method of the present invention can improve the defects encountered by prior arts. In addition, the method of the present invention can provide a suitable mark and the sample can avoid unnecessary damage by using the specific metallic mark "==" during the preparing process. Moreover, the method of the present invention not only overcomes the difficulty in the failure analysis of the finished DRAM having a size less than 0.25 $\mu$m, but also reduces the cost for preparing an ultra-thin specimen.

The above embodiments can be modified by any skillful person in the art without departing the spirit and scope of the accompanying claims.

What is claim is:

1. A method for distinguishing a specific region in a sample to be observed by a microscope, comprising steps of:
   (a) forming a first concavity on a first side of said specific region by a focus ion beam (FIB) technique;
   (b) forming a second concavity on a second side of said specific region opposite to said first side by said focus ion beam technique; and
   (c) filling said first concavity and said second concavity with a first metallic packing and a second metallic packing respectively for defining said specific region to be observed.

2. The method according to claim 1 wherein said method further includes a step of forming a third concavity on said first side of said specific region and a fourth concavity on said second side of said specific region, and then filling said third concavity and said fourth concavity with a third metallic packing and a fourth metallic packing respectively.

3. The method according to claim 2 wherein said first concavity and said third concavity are positioned between said second concavity and said fourth concavity.

4. The method according to claim 2 wherein said first concavity is positioned between said second concavity and said fourth concavity, and said fourth concavity is positioned between said first concavity and said third concavity.

5. The method according to claim 2 wherein after said step (c), said method further includes a step of (d1) polishing one side of said sample at a relatively higher polishing rate till said first metallic packing is partially polished.

6. The method according to claim 5 wherein after said step (d1), said method further includes a step of (d2) polishing said one side of said sample at a relatively lower polishing rate till said first metallic packing is completely polished.

7. The method according to claim 6 wherein after said step (d2), said method further includes a step of (d3) stopping polishing said one side of said sample and then polishing the other side of said sample.

8. The method according to claim 2 wherein each of said metallic packings is made of one selected from Platinum (Pt) and Tungsten (W).

9. The method according to claim 2 wherein each of said concavities is substantially a parallelepiped having a length larger than 2 $\mu$m, a width ranged from 1 to 2 $\mu$m, and a depth ranged from 3 to 5 $\mu$m.

10. The method according to claim 2 wherein each of said concavities is extended to a silicon substrate under said specific region of said sample.

11. The method according to claim 2 wherein the distance between said first concavity and said third concavity is larger than 2 $\mu$m.

12. The method according to claim 1 wherein said specific region has a width of about 0.5 $\mu$m.

13. The method according to claim 1 wherein said step (c) is executed by a sputtering technique.

14. The method according to claim 1 wherein said microscope is one selected from the group consisting of an optical microscope (OM), a transmission electron microscope (TEM), and a scanning electron microscope (SEM).

* * * * *